(12) United States Patent
Chou et al.

(10) Patent No.: US 7,268,865 B2
(45) Date of Patent: Sep. 11, 2007

(54) METHOD OF DETECTING FOREIGN OBJECTS FOR DISPLAY PANEL FABRICATION

(75) Inventors: Shuei-De Chou, YunLin Hsien (TW); Tzu-Chien Chiang, Panchiao (TW)

(73) Assignee: Chunghwa Picture Tubes, Ltd., Taipei (TW)

( * ) Notice: Subject to any disclaimer, the term of this patent is extended or adjusted under 35 U.S.C. 154(b) by 44 days.

(21) Appl. No.: 11/230,725

(22) Filed: Sep. 21, 2005

(65) Prior Publication Data

US 2006/0109456 A1 May 25, 2006

(30) Foreign Application Priority Data

Sep. 22, 2004 (TW) ............... 93128726 A

(51) Int. Cl.
*G01N 21/00* (2006.01)
(52) U.S. Cl. ................. 356/237; 356/152.2; 356/152.3
(58) Field of Classification Search ............. 356/237.3, 356/32, 150, 138, 399, 153, 152.3, 152.2, 356/400
See application file for complete search history.

(56) References Cited

U.S. PATENT DOCUMENTS

| 4,991,964 | A  | * | 2/1991 | Forgey et al. ............... 356/613 |
| 6,833,913 | B1 | * | 12/2004 | Wolf et al. ............... 356/237.2 |
| 2004/0169850 | A1 | * | 9/2004 | Meeks ..................... 356/237.2 |

* cited by examiner

*Primary Examiner*—Gregory J. Toatley, Jr.
*Assistant Examiner*—Tri Ton
(74) *Attorney, Agent, or Firm*—Birch, Stewart, Kolasch & Birch, LLP

(57) ABSTRACT

A method of detecting foreign objects in display manufacturing process, wherein the method comprising steps as flows: First a laser source and a laser detector are provided on a first side of a target to be measured, wherein the laser detector is supported by an adjustable gauge to provide the laser detector both horizontal and vertical movement. Then, a reflector located is provided on a second side of the target, wherein a laser beam coming from the laser source passes through a detecting position over the surface of the target, and is reflected to the laser detector by the reflector. Subsequently the intensity of the reflected laser beam is received and measured of by the laser detector.

21 Claims, 1 Drawing Sheet

METHOD OF DETECTING FOREIGN OBJECTS FOR DISPLAY PANEL FABRICATION

RELATED APPLICATIONS

The present application is based on, and claims priority from, Taiwan Application Serial Number 93128726, filed Sep. 22, 2004, the disclosure of which is hereby incorporated by reference herein in its entirety.

FIELD OF THE INVENTION

The present invention relates to a method for detecting foreign object, and more particularly, relates to a method of detecting foreign objects on a working stage or a substrate for a display panel fabrication.

BACKGROUND OF THE INVENTION

Generally, keeping a working stage and the surface of a substrate clean is crucial for fabricating a liquid crystal display (LCD), for any particle existing thereon may degrade the quality and stability of the process, or even result in damages to the working stage and the product.

Especially, during an alignment film coating process of the LCD back-end process, the foreign objects existing on the working stage or on the surface of the substrate will deter the coating process from being smoothly performed, thus effecting the quality of the alignment film and lowering the quality control of the LCD. Further, the foreign particles may cause damages to coating rollers or other equipment, and even break a glass substrate, thus effecting productivity and reducing the operation life of the equipment.

Hence, besides keeping the working stage and the surface of the substrate clean, a foreign objects detecting step is also needed. Generally, before the manufacturing process starts, the foreign objects detecting step is first performed onto the working stage or the substrate surface, wherein if any foreign object is detected, then the manufacturing process is stopped, thus effectively preventing the foreign objects on the working stage or the substrate surface from damaging the products and equipment.

The conventional foreign objects detecting step uses a laser beam or diffusion light to perform detection on the working stage or the substrate surface, wherein the foreign objects are monitored in accordance with the intensity changes of light diffusion, reflection or refraction. However, by using the diffusion light, the object size that can be identifies is rather limited, and the precision of detecting the foreign objects thereby is not sufficient to be suitable us in a display panel or even semiconductor manufacturing process. Therefore, the current foreign objects detecting method mostly adopts the laser source so as to increase the precision of detecting the foreign objects.

However, the current foreign objects detecting methods all place a laser source above a working stage or a substrate, and directly irradiate the surface of the working stage or substrate, and then observe the states of the laser light before and after reflection or diffusion and refraction. The laser light is interfered simultaneously by the working stage, the substrate and the foreign objects, and thus, if the refractive indexes of the foreign objects located on the working stage and the substrate are close to those of the working stage and the substrate, then the foreign objects cannot be detected. For example, the refractive index of the glass scrap is the same as that of the glass substrate. Further more, since the even smaller foreign particles have less apparent degrees of interference against the laser light, and are susceptible to the inference from the working stage and the substrate, they are hardly to be detected. Further, the laser light has to be frequently calibrated effecting accordance with the materials forming the working stage and the substrate, thus resulting in many errors of the actual measurement and limiting the detection precision.

SUMMARY OF THE INVENTION

Therefore, it is desirable to provide a method for promoting the accuracy and precision for detecting foreign objects, thereby benefiting the monitoring of foreign objects on the working stage or a substrate.

One aspect of the present invention is to provide a method for detecting foreign objects on the working stage or a substrate for manufacturing a LCD or a semiconductor circuit. A laser beam passing across the top surface of a working stage or a substrate for a LCD fabrication is provided, and is reflected to form a feed back laser beam by a reflector. Then, the intensity of the feed back laser beam by a reflector is determined. If there exists any foreign objects, the intensity of the feedback laser beam should be attenuated due to refraction or absorption by the foreign objects.

According to the aspect of the present invention, an improved method used for detecting foreign objects on the working stage or a substrate is provided for manufacturing a LCD or a semiconductor circuit. In accordance with a preferred embodiment of the present invention, the method used for detecting foreign objects on a target to be detected comprises the steps as follows: At first, a laser device having a laser source and a laser detector is installed on one side of the target, and a reflector aligned the laser detector is installed on the other side of the target. Then, a laser beam provided by the laser source passes across the surface of the target and is reflected back to the laser detector by the reflector, and thus a feedback light beam is formed by the reflector. Subsequently, the intensity of the feedback laser beam is measured to determine if any laser intensity is attenuated, so as to determine, if there is any foreign objects existing on the surface of the target.

In the preferred embodiments of the present invention, the target can be referred to a working stage or a substrate for manufacturing a LCD. The laser device is mounted on an adjustable gauge to adjust both horizontal and vertical positions of the laser detector precisely, so that the laser beam coming from the laser device can pass through a predetermined position over the surface of the target to a reflecting mirror. Then, a feedback light beam is formed by the reflecting mirror and returns to the laser device. In accordance with the difference between the intensity of the laser beam and the intensity of the feedback light beam, any foreign objects existing on the surface of the target can thus be recognized.

According to the method disclosed in the present invention, since the intensity of the laser beam may be refracted or absorbed only by the foreign objects existing on the surface of the target, and is not affected by the target at all, the existence of the foreign objects can be detected clearly, and even the foreign objects having similar refractivity with the target also can be accurately detected thereby.

Therefore, the application of the foreign objects detecting method of the present invention, not only can increase the accuracy and precision of detecting foreign objects, but also can reduce the frequency of performing a calibration step in accordance with the changes of the target to be detected, and further can prevent the manufacturing process from being damaged and affected by the existence of the foreign objects, thus maintaining the stability of the manufacturing process and the product yield; reducing the loss of the fabrication cost; and elongating the operation life of the processing equipment.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the following detailed description and the accompanying drawings, which are by way of illustration only, and thus are not limitative of the present invention, and wherein.

DETAILED DESCRIPTION OF THE PREFERRED EMBODIMENTS

Figure 1:
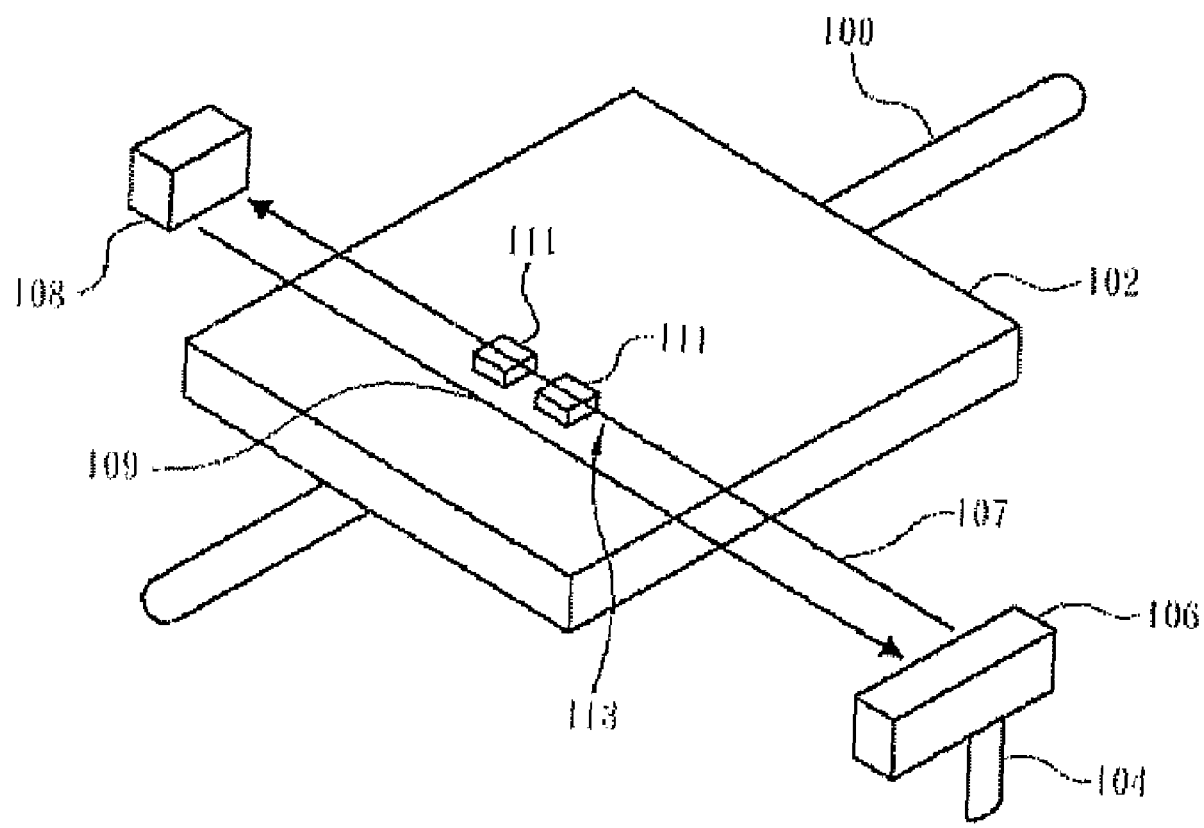
FIG. 1 regards a method for detecting the foreign objects on a working stage or a substrate during a LCD fabrication, in accordance with the preferred embodiment of the present invention.

An improved method used for detecting foreign objects on a target to be detected is provided. In accordance with a preferred embodiment of the present invention, a laser device having a laser source and a laser detector is installed on one side of a target, and a reflector aligned the laser detector is installed on the other side of the target. Then, a laser beam provided by the laser source passes across the surface of the target and is reflected back to the laser detector by the reflector, wherein a feedback light beam is formed by the reflector. Subsequently, the intensity of the feedback laser beam is measured and compared to the intensity of the laser beam, so as to determine if the laser intensity is attenuated. In accordance with the result, whether there is any foreign object existing on the surface of the target can thus be recognized.

The foregoing aspects and many of the attendant advantages of this invention will become more readily appreciated by reference to the following detailed embodiment:

EMBODIMENT

The following detailed embodiment is an improved method for detecting foreign objects on a working stage or a substrate is provided for a LCD fabrication.

FIG. 1 is about a method for detecting the foreign objects on a working stage or a substrate during a LCD fabrication, in accordance with the preferred embodiment of the present invention. A working stage 102 is horizontally mounted on a movable carrier 100. An adjustable gauge 104 located on one side of the working stage 102 is provided, wherein the adjustable gauge 104 can be adjusted along both horizontal and vertical directions. A laser device 106 having a laser source and a laser detector is mounted on the adjustable gauge 104, wherein the laser source can provide a long-distance laser beam and the laser detector can receive and measure a long-distance laser beam. A reflector 108, such as a reflecting mirror is installed in alignment with the laser detector of the laser device 106. A laser beam 107 that is parallel to the top surface of the working stage 102 is provided by the laser source of the laser device 106, and then the laser beam is reflected back to form a feedback laser beam 109 by the reflector 108. The intensity of the feedback laser beam 109 is measured and compared to that of the laser beam 107 by the laser device 106.

The position of the laser device 106 can be adjusted along both horizontal and vertical directions via the gauge 104 so as to control the positions 113 where the laser beam 107 passing through above the working stage 102. The movable carrier 100 horizontally driving the working stage 102 can make the laser beam 107 passing through any position on the working stage 102.

The reflector 108 is used to reflect the laser beam 107 back to the laser device 106 so as to form the feedback laser beam 109. The laser detector of the laser device 106 is used for receiving the feedback laser beam 109; measuring the intensity of the feedback laser beam 109; and comparing the intensity of the feedback laser beam 109 with the intensity of the laser beam 107. The difference between the intensity of the laser beam 107 and that of the intensity of the feedback laser beam 109 for a intensity attenuation value used for determining if there are any foreign objects on the surface of the working stage 102.

The reflected laser beam 109 is not refracted or absorbed by the working stage 102. Thus, when no foreign objects exist on the surface of the working stage 102, the laser beam 107 can be reflected back to the laser device 106 by the reflector 108 with little loss, so that the intensity of the feedback laser beam 109 and that of the laser beam 107 are substantially the same. When foreign objects 111 exist on the surface of the working stage 102, the reflected laser beam 109 is refracted or absorbed by the foreign objects existing thereon, and the reflected laser intensity is attenuated with certain degrees of attenuation. Consequently, the existence of foreign objects 111 on the surface of the working stage 102 can be recognized by the principle described above.

A predetermined laser intensity attenuation value is provided as a condition to determine if there are any foreign objects on the surface of the working stage 102. When the intensity attenuation value is lower than the predetermined laser intensity attenuation value, it is indicated that there are foreign objects on the surface of the working stage 102, and the processing apparatuses or the processing control system has to be shutdown immediately.

Although in the present embodiment uses the movable carrier 100 horizontally to move the working stage 102, for detecting every position on the working stage 102, yet the present invention also can horizontally change the position of the laser device to accomplishing the detection throughout every position on the working stage 102. Furthermore, the method provided by the present invention may not be restricted for detecting the foreign objects on the working stage or the substrate for manufacturing a LCD. The present method may be suitable for any kind of working stage or substrate.

Accordingly, the laser beam merely passes across the surface of the target to be detected, so that the intensity of the laser beam is merely refracted or absorbed by the foreign objects existing on the surface of the target, and is not affected by the target at all. For example, since the working stage or the substrate of a LCD panel refracts little laser, the foreign objects having similar refractivity with the glass substrate, such as glass scraps can be identified easily, and particles refracts little laser can also be identified more easily. Furthermore, different laser beams can be applied in accordance with the context of the manufacture process to enhance the precision of the present method. For example, various laser beams with different intensities or wavelengths can be applied in accordance with the properties of the particles likely generated during the manufacture process, so as to enhance the reliability of the present method.

It must be appreciated that, since the working stage or the substrate of a LCD panel to be detected cannot affect the laser beam passing across the surface thereon, basically it is not necessary to change the laser beam when the material thereof is changed.

In some embodiment of the present invention, the present method applies a laser beam across a working stage to identify foreign objects rather applies a laser beam on a working stage directly. This can avoid the measuring variation due to vacuum holes that are set on the working stage for holding a substrate.

Therefore, the present invention can be applied in any kind of working stage or substrate for manufacturing a LCD or a semiconductor circuit to provide an improved method with more precision for detecting the existence of foreign objects. The improvement of the detecting results can prevent the apparatus and products from damage due to the impact of foreign objects during the manufacturing process, so as the yield can be increased, and the operation life of the apparatus can be elongated. For example the impact of a glass scrap occurs on a LCD panel during the process for forming an alignment layer may be reduced, as the foreign objects exists on the substrate is precisely identified.

As is understood by a person skilled in the art, the foregoing preferred embodiments of the present invention are illustrated of the present invention rather than limiting of the present invention. It is intended to cover various modifications and similar arrangements included within the spirit and scope of the appended claims, the scope of which should be accorded the broadest interpretation so as to encompass all such modifications and similar structure.

What is claimed is:

1. A method of detecting foreign objects in a display panel fabrication, comprising the steps of:
   mounting a laser source and a laser detector on a first side of a target to be detected, wherein the laser detector is mounted on an adjustable gauge to adjust both horizontal and vertical positions of the laser detector;
   providing a reflector located on a second side of the target;
   using the laser source to provide a laser beam which passes through a detecting position located above the target and then moves on to the reflector;
   reflecting the laser beam with the reflector to form a feedback light beam which passes through the detecting position and moves directly on to the laser detector;
   receiving the feedback light beam with the laser detector;
   measuring the intensity of the feedback light beam; and
   comparing the intensity of the feedback light beam with a predetermined laser intensity attenuation value to determine if any foreign object exists on the surface of the target.

2. The method of claim 1, wherein the target is a working stage.

3. The method of claim 1, wherein the target is a substrate.

4. The method of claim 1, wherein the reflector is a reflecting minor used for reflecting the laser beam to form the feedback light beam.

5. The method of claim 1, wherein the laser beam is a long-distance laser beam.

6. The method of claim 1, wherein the difference between the intensity of the laser beam and the intensity of the feedback light beam stands for an intensity attenuation value.

7. The method of claim 6, wherein, when the intensity attenuation value is larger than a predetermined attenuation value, it indicates that at least one foreign object exists on the target.

8. The method of claim 1, further comprising:
   moving the target or the laser detector to detect foreign objects at other positions on the target.

9. A method of detecting foreign objects in a display panel fabrication, applied for detecting a surface of a working stage, comprising the steps of:
   providing a gauge on a first side of the working stage;
   mounting a laser source and a laser detector on the gauge;
   providing a reflector located on a second side of the working stage;
   using the laser source to provide a laser beam which passes through a detecting position above the surface of the working stage and then moves on to the reflector;
   reflecting the laser beam with the reflector to form a reflected laser beam which passes through the detecting position and moves directly on to the laser detector;
   receiving the reflected laser beam the laser detector; and
   measuring and comparing the intensity of the reflected laser beam with a predetermined laser intensity attenuation value so as to determine if any foreign object exists on the surface of the working stage.

10. The method of claim 9, wherein the gauge is used for adjusting both horizontal and vertical positions of the laser detector.

11. The method of claim 9, wherein the reflector is a reflecting mirror.

12. The method of claim 9, wherein the difference between the intensity of the laser beam and the intensity of the reflected laser beam stands for an intensity attenuation value of the laser beam.

13. The method of claim 12, wherein, when the intensity attenuation value is larger than a predetermined attenuation value, it indicates that at least one foreign object exists on the working stage.

14. The method in accordance with claim 9, further comprising moving the working stage or the laser detector to detect foreign objects throughout every position over the working stage.

15. A method of detecting foreign objects on a substrate during a display manufacturing process, comprising the steps of:
   providing a gauge on a first side of the substrate to be measured;
   mounting a laser source and a laser detector on the gauge;
   providing a reflector located on a second side of the substrate;
   providing a laser beam which comes from the laser source to pass through a detecting position over the surface of the substrate, and is reflected directly on to the laser detector by the reflector;
   receiving the laser beam reflected from the reflector with the laser detector; and
   measuring and comparing the intensity of the reflected laser beam with a predetermined laser intensity attenuation value to determine if any foreign object exists on the surface of the target.

16. The method in accordance with claim 15, wherein the gauge is adjustable to provide the laser detector with both horizontal and vertical movement.

17. The method in accordance with claim 15, wherein the substrate is a glass panel.

18. The method in accordance with claim 15, wherein the reflector is a mirror.

19. The method in accordance with claim 15, wherein the difference between the intensity of the laser beam and that of the reflected laser beam can be used as a parameter for detecting foreign objects.

20. The method in accordance with claim 19, wherein; when the parameter is larger than a predetermined parameter, it indicates that at least one foreign object exists on the substrate.

21. The method in accordance with claim 9, further comprising moving the working stage or the laser detector to detect foreign objects throughout every position over the substrate.

* * * * *